(12) United States Patent
Mc Clay et al.

(10) Patent No.: US 6,288,111 B1
(45) Date of Patent: *Sep. 11, 2001

(54) COMBINATION CISPLATIN/TAMOXIFEN THERAPY FOR HUMAN CANCERS

(75) Inventors: Edward F. Mc Clay, Encinitas; Stephen B. Howell, Del Mar, both of CA (US)

(73) Assignee: Research Development Foundation, Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/484,024

(22) Filed: Jun. 7, 1995

Related U.S. Application Data

(62) Division of application No. 08/023,271, filed on Feb. 26, 1993.

(51) Int. Cl.⁷ .................. A61K 31/28; A61K 31/135
(52) U.S. Cl. ............................. 514/492; 514/648
(58) Field of Search .................................. 514/492, 648

(56) References Cited

PUBLICATIONS

Rakel, Conn's Current Therapy, W. B. Saunders Co.,Philadelphia, Pa.,p. 151, Apr. 1992.*
Harwett et al., Wow–Serial (1991) Clinical Oncology Society of Australia, Inc., p. 129. The Original Reference to Follow.*

* cited by examiner

*Primary Examiner*—Jerome D. Goldberg
(74) *Attorney, Agent, or Firm*—Benjamin Aaron Adler

(57) ABSTRACT

The present invention provides a novel composition of matter useful for the treatment of a wide variety of human cancers. The novel composition is synergistic and cytotoxic and comprised of platinum containing antineoplastic agent and tamoxifen. The present invention also provides for methods of treating cancer. That is, the present invention provides a novel method of treating non-melanoma cancers used the novel pharmacologic combination of the present invention. Other embodiments of the invention provide novel methods of reducing or overcoming resistance that develops to platinum containing antineoplastic agents, such as, cisplatin.

2 Claims, 7 Drawing Sheets

COMBINATION CISPLATIN/TAMOXIFEN THERAPY FOR HUMAN CANCERS

This is a division of application Ser. No. 08/023,271 filed on Feb. 26, 1993,

BACKGROUND OF THE INVENTION

1. Field of the Invention

The present invention relates generally to the fields of medical oncology and the pharmacotherapy of human cancers. More specifically, the present invention relates to novel methods of treating cisplatin resistant or cisplatin non-resistant cancers using a combination of tamoxifen and cisplatin.

2. Description of the Related Art

The treatment of cancer patients with platinum coordination complex antineoplastic agents, such as cis-diamminedichloroplatinum (II) (cisplatin) has increased substantially in the last decade. Cisplatin is a antineoplastic agent that has proved useful in the treatment of multiple malignancies including testicular cancer, ovarian cancer, and small cell lung cancer. The mechanism of action is currently unknown but may be related to the ability of cisplatin to bind to DNA and form various types of inter- and intrastrand crosslinks that possibly interfere with both DNA and RNA synthesis.

Cancer patients eventually become resistant to treatment with platinum coordination complexes, such as cisplatin. If the patient dies of metastatic cancer, the cells of the metastatic foci are usually also characterized by their extreme resistance to single or combinations of the available chemotherapeutic drugs. In general, drug resistant tumors can be classified as temporary or permanent. The mechanism of resistance to cisplatin is unclear but may be related to decreased drug accumulation, elevation of intracellular concentrations of metallothioneines or glutathione which bind and inactivate cisplatin, or to decreased cisplatin-DNA adduct formation or repair.

Tamoxifen is an antiestrogen agent that has been used extensively in the treatment of women with breast cancer. The accepted mechanism of action of tamoxifen in breast cancer is via antagonism of the estrogen receptor leading to interference with estrogen induced cell growth.

One of the major problems in cancer therapy today is the ability of tumor cells to develop resistance to chemotherapeutic agents. This is particularly frustrating because a patient initially responds to the antineoplastic drug, such as cisplatin.

The prior art remains deficient in the absence of an efficient and efficacious method of preventing resistance or overcoming established resistance to platinum coordination complex anti-neoplastic agents. In addition, the prior art is deficient in the lack of an effective method of potentiating the cytotoxic effects of platinum coordination complex anti-neoplastic agents.

SUMMARY OF THE INVENTION

The present invention provides a novel composition of matter for the treatment of human cancers. In addition, the present invention provides novel methods of reducing and/or overcoming resistance to platinum chemotherapeutic agents.

The present invention demonstrates a novel pharmacodynamic effect of tamoxifen (TAM), namely the ability to delay the emergence of resistance to cisplatin or cis-diamminedichloroplatinum (DDP) for cell lines representative of 2 important types of human malignancy, melanoma and ovarian carcinoma. It has not previously been demonstrated that TAM could alter the processes that underlie the development of resistance.

In one embodiment of the present invention, there is provided a composition of matter for the treatment of non-melanoma cancers, wherein the composition comprises a platinum anti-neoplastic compound and tamoxifen, wherein the platinum anti-neoplastic compound and tamoxifen exert a synergistic anti-tumor effect on the non-melanoma cancer.

In another embodiment of the present invention, there is provided a method of treating a non-melanoma cancer comprising administering to an individual having a non-melanoma cancer, a pharmacological dose of a platinum anti-neoplastic compound and tamoxifen, wherein the platinum anti-neoplastic compound and tamoxifen exert a synergistic anti-tumor effect on the non-melanoma cancer.

In yet another embodiment of the present invention, there is provided method of reducing resistance to platinum anti-neoplastic compounds in an individual having a neoplastic disease comprising administering tamoxifen to an individual, wherein the individual is susceptible to developing resistance to platinum anti-neoplastic compounds.

In still yet another embodiment of the present invention, there is provided method of overcoming resistance to platinum anti-neoplastic agents in an individual having a neoplastic disease, comprising administering tamoxifen to the individual.

In still yet another embodiment of the present invention, there is provided a method of killing non-melanoma neoplastic cells in bone marrow, comprising the steps of removing bone marrow from an individual having a neoplastic disease; contacting said bone marrow with a cytocidally effective dose of a platinum containing antineoplastic compound and tamoxifen, and returning said contacted bone marrow to said individual.

Other and further objects, features and advantages will be apparent from the following descriptions of the presently preferred embodiments in the invention which are given for the purpose of disclosure and when taken in conjunction with the accompanying drawings.

BRIEF DESCRIPTION OF THE DRAWINGS

The drawings are not necessarily to scale. Certain features of the invention may be exaggerated in scale or shown in schematic form in the interest of clarity and conciseness.

DETAILED DESCRIPTION OF THE INVENTION

Figures 1A, 1B, 1C:
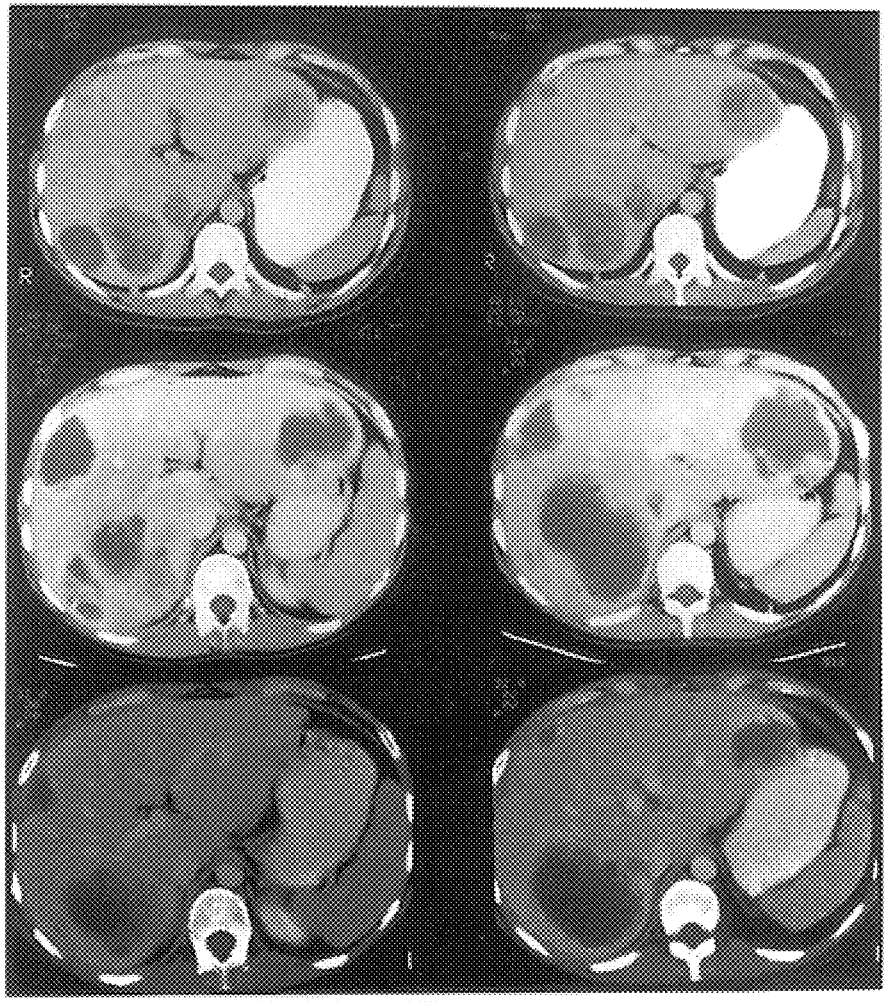
FIG. 1 shows photographs of computerized tomograms for a patient. The scans show 2 consecutive levels through the liver; 1A) prior to therapy; 1B) after 1 cycle of DDP alone; and 1C) after 1 cycle of TAM/DDP.

The present invention provides a composition of matter for the treatment of non-melanoma cancers, wherein said composition comprises a platinum anti-neoplastic compound and tamoxifen, wherein said platinum anti-neoplastic compound and tamoxifen exert a synergistic anti-tumor effect on said non-melanoma cancer. Synergism or synergistic as used to describe the composition and methods of the present invention means a greater than additive biological effect. Thus, to state that tamoxifen is synergistic with a platinum containing antineoplastic compound means that the combination, in any form, produces greater cytotoxicity that either drug alone.

The novel composition of matter of the present invention may be used to potentiate anti-neoplastic activity in a wide variety of non-melanoma cancers. Preferably, the novel composition of matter is used to treat ovarian carcinoma, small lung cell carcinoma, bladder cancer, testicular cancer and squamous cell cancer of the head and neck.

Generally, the platinum containing anti-neoplastic agent of the novel composition of matter may be any platinum coordination complex that has an anti-neoplastic effect. Most preferably, the platinum containing anti-neoplastic agent of the composition of the present invention is cisplatin or carboplatin (CBDCA) but could include tetraplatin and topotecan.

Generally, the concentration of the platinum containing anti-neoplastic agent and of tamoxifen in the novel composition of the present invention may be that which allow for a synergistic cytotoxic effect of the combination. Preferably, the amount of the platinum containing anti-neoplastic agent is from about 1 $\mu$M to about 10 $\mu$M. Similarly, the concentration of tamoxifen administered as a component of the novel composition or in the methods of the present invention is from about 0.1 $\mu$M to about 2.0 $\mu$M.

Tamoxifen is the preferred antiestrogen useful in the composition and methods of the present invention. However, a person having ordinary skill in this art would readily recognize that other antiestrogens and tamoxifen-like compounds may be useful as part of the composition or in the methods of the present invention. For example, DDPE (N,N-diethyl-2-[4-(phenylmethyl)phenoxy) ethanamine is an antagonist of antiestrogen binding sites and microsomal and intranuclear binding sites. DPPE synergizes with cisplatin to produce a synergistic cytotoxic effect and can also overcome cisplatin resistance. Concentrations of DPPE between 1 $\mu$M and 10 $\mu$M is desirable.

Administration of the novel composition may be by oral, intravenous, or any other suitable means. The platinum containing antineoplastic compound may be co-injected with tamoxifen. Alternatively, the platinum containing antineoplastic compound may be administered separately to the tamoxifen. A person having ordinary skill in this art would readily recognize that the composition and methods of the present invention may be administered in a variety of ways to achieve synergistic cytotoxicity or reduction of resistance.

The dosage administered is dependent upon the age, weight, kind of concurrent treatment, if any, and nature of the cancer. The effective composition useful in the methods of the present invention may be employed in such forms as capsules, tablets, liquid solutions, suspensions or elixirs for oral administration or sterile liquid forms such as solutions, suspensions or emulsions. Any inert carrier is preferably used, such as saline or phosphate buffered saline or any such carrier in which the compounds used in the methods of the present invention have suitable solubility properties.

The novel composition of matter of the present invention may be administered in a pharmaceutically acceptable carrier. The pharmaceutically acceptable carrier is any solvent with which the composition of the present invention is compatible and which is non-toxic to the individuals treated at the amounts administered. A pharmacological dose of the novel composition of the present invention useful in the methods of the present invention is that amount of the platinum containing antineoplastic agent and tamoxifen which achieves a synergistic cytotoxic effect on non-melanoma tumors. Similarly, when used alone to treat resistance to platinum containing antineoplastic agents, a pharmacological dose of tamoxifen is that which reduces or overcomes resistance to platinum containing antineoplastic agents in individuals having a neoplastic disease.

The present invention also provides a method of treating a non-melanoma cancer in vivo or in vitro comprising administering to an individual having said non-melanoma cancer, a pharmacological dose of a platinum anti-neoplastic compound and tamoxifen, wherein said platinum anti-neoplastic compound and tamoxifen exert a synergistic anti-tumor effect on said non-melanoma cancer. The platinum containing antineoplastic compound is preferably cisplatin or carboplatin.

Generally, the platinum containing antineoplastic compound and tamoxifen may be administered in any order. Preferably, tamoxifen is administered prior to the administration of the platinum containing antineoplastic compound. Most preferably, tamoxifen is administered 24 hours prior to the administration of the platinum containing antineoplastic agent.

The present invention also provides a method of reducing resistance to platinum anti-neoplastic compounds in an individual having a neoplastic disease comprising administering tamoxifen to said individual, wherein said individual is susceptible to developing resistance to platinum anti-neoplastic compounds. Similarly, the present invention also provides a method of overcoming resistance to platinum anti-neoplastic agents in an individual having a neoplastic disease, comprising administering tamoxifen to the individual.

Generally, the methods of reducing or overcoming platinum containing anti-neoplastic agent resistance of the present invention may be useful in the treatment of any neoplastic disease. Preferably, these methods may be used to treat melanoma, ovarian carcinoma, small cell lung carcinoma, bladder cancer, testicular cancer and squamous cell cancer of the head and neck.

The methods of reducing or overcoming resistance to platinum containing anti-neoplastic agents may be generally useful in treating resistance that occurs to any platinum coordination complex anti-neoplastic chemotherapeutic agent. Preferably, the platinum anti-neoplastic compounds are selected from the group consisting of cisplatin and carboplatin.

Another embodiment of the present invention is a method of killing non-melanoma neoplastic cells in bone marrow, comprising the steps of removing bone marrow from an individual having a neoplastic disease; contacting said bone marrow with a cytocidally effective dose of a platinum containing antineoplastic compound and tamoxifen, and returning said contacted bone marrow to said individual.

EXAMPLE 1

In Vivo Utility of DDP and Tamoxifen Combination

A clinical trial was conducted in which patients were initially treated with DDP alone. Once patients were found to be resistant to single agent DDP, they were treated with the combination of TAM and DDP to determine whether the addition of TAM could overcome established DDP resistance.

From June 1990 to March 1992, 24 patients who had not had prior DDP or TAM treatment were treated. Entry requirements included histologically documented melanoma, measurable disease, signed informed consent, and no anti-tumor therapy during the previous 4 weeks. Patients were required to have normal hematologic and renal function, an Eastern Cooperative Oncology Group (ECOG) performance status of 0–2 and an estimated survival of at least 3 months. Patients with a previous history of deep venous thrombosis or pulmonary embolism were excluded.

A complete response was defined as the complete disappearance of all evidence of disease for at least 4 weeks. A partial response was a decrease in the mean diameter of the target lesion by 50% or more lasting at least 4 weeks. A mixed response was a decrease in the diameter of some target lesions of 50% or more while others remained stable or increased in size. A stable disease was defined as a <50% decrease or <25% increase in the size of target lesions for at least 2 months without the growth or appearance of other lesions. A progressive disease was defined as an increase in the size of target lesions by 25% or more. Patients were considered to be resistant to DDP if they had progressive disease after receiving one cycle of DDP or stable disease after receiving two cycles of treatment with DDP alone.

DDP, 100 mg/ml, was mixed in sufficient 0.9% sodium chloride solution to produce a final concentration of at most 1 mg/ml and was administered over 2 hours. Pre-treatment hydration consisted of 1 liter of 5% dextrose/0.45% saline containing 20 mEq of potassium chloride and 2 g magnesium sulfate administered over 4 hours. Post-DDP hydration consisted of 2 liters of 5% dextrose/0.45% saline containing 20 mEq of potassium chloride and 2 g magnesium sulfate administered at 150 ml/hr. Patients were retreated every 3 weeks. On cycles where TAM was administered, 40 mg p.o. four doses per day were given on day 1 followed by 20 mg p.o. daily thereafter. The initial 7 patients were treated with a combination of lorazepam, metaclopramide, benadryl and dexamethasone to control nausea and vomiting. Subsequent patients received an ondansetron-based regimen.

Patients were initially treated with DDP as a single agent and were evaluated for response every 3 weeks. Patients whose disease progressed after one cycle of DDP alone were candidates for treatment with DDP plus TAM, as were patients whose disease was stable after 2 cycles of DDP alone. Patients responding to DDP alone continued to receive single agent DDP treatment until either a complete response was achieved or progressive disease supervened.

Pre-treatment characteristics are listed in Table 1. Only 2 patients had previously received chemotherapy (1 of whom also received immunotherapy) and only 1 patient had received prior radiation therapy. The majority of patients had an excellent performance status and the metastatic pattern was as expected for melanoma.

TABLE 1

| Patient characteristics | |
| --- | --- |
| Male/Female | 16/8 |
| Median age (years) | 58 |
| Range | 30–77 |
| Performance status (ECOG) | |
| 0 | 12 |
| 1 | 8 |
| 2 | 4 |
| 3 | 0 |
| 4 | 0 |
| Sites of Metastatic Disease | |
| Lymph node | 11 |
| Skin | 10 |
| Lung | 7 |
| Liver | 7 |
| Adrenal gland | 2 |
| Gastrointestinal | 1 |
| Bone | 1 |
| Brain | 1 |
| Previous Treatment | |
| None | 21 |
| Chemotherapy or Immunotherapy | 1 |
| radiation | 1 |

Response data is listed in Table 2. All 24 patients were evaluated for response to DDP alone. One patient had a complete response while 2 patients demonstrated a partial response. The complete response lasted more than 15 months. One of the patients with a partial response has remained stable off treatment for 6+ months, while the other patient progressed after 4 months and went on to TAM/DDP treatment. The patient who had a complete response with DDP alone had multiple subcutaneous nodules as the only site of disease. The partial responses were seen in patients with lung and retroperitoneal lymph node disease.

TABLE 2

Responses to treatment with DDP or a DDP/TAM combination

| | Cisplatin | Tamoxifen/Cisplatin |
| --- | --- | --- |
| Total Patients | 24 | 20[2] |
| Complete Response (%) | 1 (4%) | 0 |
| Partial Response (%) | 2 (8%) | 3 (15.5%) |
| Mixed Response (%) | 0 | 3 (15.5%) |
| Progressive Disease | 19[1] | 13 |
| Stable Disease | 2 | 0 |
| Not Evaluable | 0 | 3[3] |

[1]Two patients refused DDP/TAM
[2]Includes 1 patient with a PR to DDP alone
[3]One suicide, 2 patients too early.

Twenty of the 24 patients initially treated with DDP alone were treated with the combination of TAM and DDP. Two patients refused the combination therapy due to unacceptable toxicity while receiving DDP alone. The patient attaining a complete response was not offered further therapy and one of the 2 patients attaining a partial response remained stable off treatment for 6+ months and did not received combination treatment. Nineteen of these 20 patients were evaluated for response. One patient committed suicide after receiving the combination of TAM and DDP but prior to evaluation for response.

Figure 2A:
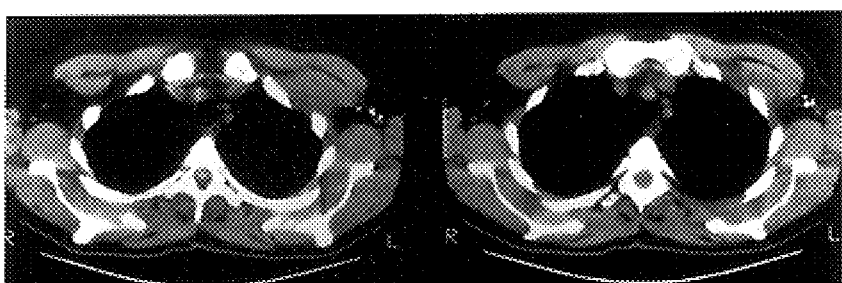
FIG. 2 shows photographs of computerized tomograms for another patient. The scans show 2 consecutive levels through the chest. The arrow points to a soft tissue mass adjacent to the rib. 2) Prior to therapy; 2B) after 2 cycles of DDP alone; and 2C) after 1 cycle of TAM/DDP.
Figure 2B:
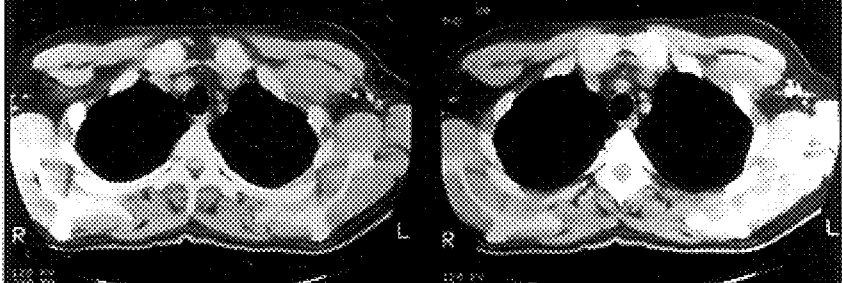
Figure 2C:
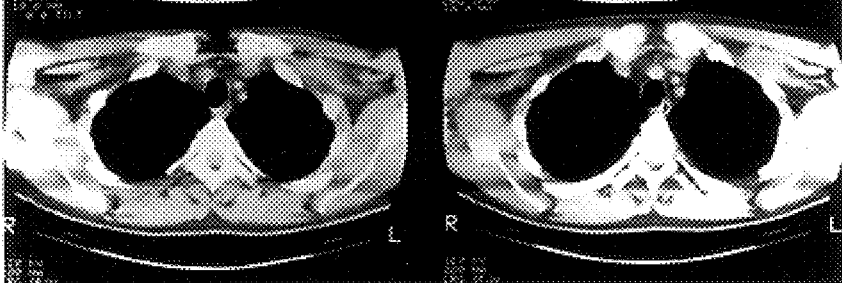

Of the 19 evaluated patients, 17 had progressive disease and 2 had stable disease while receiving single agent DDP therapy. Three patients achieved a partial response while 3 others had a mixed response for an overall response rate of 35%. This permitted rejection of the null hypothesis that no responses would be observed ($p<0.001$). One patient attained a partial response with 4 cycles of TAM and DDP, and then was rendered surgically free of disease. Response to the combination of TAM and DDP was seen in patients with live (FIG. 1), bone, and soft tissue disease (FIG. 2). The partial responses ranged from 6 to 8 weeks. Patients who did not respond or who progressed after responding, as well as those who demonstrated a mixed response, were treated with the full four drug regimen of TAM/DDP/carmustine/dacarbazine. There were no responses among the 12 patients treated with this regimen.

The toxicities encountered with the DDP/TAM combination treatment are listed in Table 3. Hematologic toxicity with either DDP alone or DDP in combination with TAM was modest with no grade 3 or 4 neutropenia or thrombocytopenia. No increased toxicity was noted with the addition of TAM to single agent DDP. Similarly, nephrotoxicity was uncommon and unaffected by the administration of TAM. This regimen did produce a difficulty for some patients with nausea and vomiting. While TAM administration did not increase nausea or vomiting, this problem proved to be the most difficult to deal with from the patient's perspective. The addition of ondonsetron markedly reduced nausea and vomiting during hospitalization. Ototoxicity and peripheral neuropathy were uncommon. This is most likely due to the fact that few patients received more than 2 or 3 doses of DDP. One patient, who was a musician, refused further DDP based therapy after one dose due to unacceptable abnormalities in tonal perception. A second patient required a hearing aid after a total dose of 545 mg of DDP. No patients developed deep venous thrombosis or pulmonary embolus.

TABLE 3

Toxicities with DDP or DDP/TAM treatment

|  | DDP | TAM/DDP |
| --- | --- | --- |
| No. of cycles | 39 | 36 |
| Neutropenia (<1000/mm$^3$) | 0 | 0 |
| Thrombocytopenia (<50,000/mm$^3$) | 0 | 0 |
| Renal (creatinine > 2 mg/dl) | 1 | 1 |
| Nausea/Vomiting (Grade 3/4) | 13/3 | 13/3 |
| Ototoxicity (Grade 3/4) | 1/0 | 1/0 |
| Peripheral neuropathy (Grade 3/4) | 0/0 | 0/0 |

The present invention establishes that the addition of TAM to single agent DDP therapy can overcome established resistance to DDP in a significant fraction of patients with malignant melanoma. All patients who were treated with the combination of TAM plus DDP were documented to be resistant to single agent DDP therapy in that they had either progressive disease after 1 cycle of DDP or stable disease after 2 cycles. The 31% overall response rate under circumstances where no responses were expected is statistically significant ($p<0.001$).

The responses resulting from the addition of TAM were not due to an independent antitumor effect of TAM. The response rate reported for single agent TAM therapy in 203 treated melanoma patients was only 6%.

As might be expected in patients with resistant tumors, the clinical responses to the combination of TAM and DDP following failure of single agent DDP therapy were interesting from the standpoint of quality and durability. In one patient, the partial response permitted surgical removal of all remaining disease and this patient has remained in complete remission for 12+ months. The other 2 partial responses were maintained for 6 and 8 weeks, respectively. Patients with a mixed response had clearly demonstrated progression of the target lesions with single agent DDP that responded to the combination of TAM/DDP, however, other lesions either progressed or remained stable. Thus, despite the fact that TAM can sensitize resistant tumors to DDP in vivo, a person having ordinary skill in this art would readily recognize that the dose schedules are individually tailored to maximize the fraction of responding patients and the magnitude of the response.

The design of the study of Example 1 itself was biased against response and the response rate in other settings would be higher. All patients were treated with DDP alone until they were clearly resistant. DDP resistance emerges rapidly. While the concentration of DDP required to achieve one log of cell kill in the resistant cells in vitro can be achieved in patients, the concentration of TAM required to overcome resistance in vitro cannot be achieved in patients with standard doses, i.e., 20 mg/day. Chronic administration of TAM at 10 mg p.o. twice a day produces steady-state plasma concentrations in the range of 0.29 $\mu$M. However, the in vitro data (vide infra) predicts that plasma concentrations of more than 1.0 $\mu$M will be necessary in DDP resistant patients. Thus, a person having ordinary skill in this art would readily recognize that the response rate to the DDP/TAM combination may be higher in patients treated initially with a greater concentration of tamoxifen up front and that DDP resistance can be overcome by increasing the dose of both DDP and TAM.

EXAMPLE 2

In Vitro Effects of Tamoxifen and DDP

The synergy between TAM and DDP was observed with other human malignancies, the human small cell lung cancer line UMC-5 and the human ovarian carcinoma cell line 2008. As was observed within the T-289 melanoma cells, there was strong synergy between TAM and DDP with both the UMC-5 cells ($CI_{30}$-0.38) and the 2008 cells ($CI_{30}$-0.63).

If TAM can synergize with DDP to overcome DDP resistance, then TAM may also delay the development of DDP resistance by a similar mechanism. TAM can delay the development of DDP resistance in both T-289 and 2008 cells when given concurrently in cell culture.

The T-289 melanoma cell line was derived from a tumor explant and was in passage for over 7 years. The 2008 cell line is an ovarian carcinoma line derived from a patient with an ovarian serous cystadenocarcinoma (type cite). Cells were cultured in 75 cm$^2$ flasks in RPMI 1640 supplemented with 10% fetal bovine serum, 50 $\mu$g/ml gentamicin, 2 mM L-glutamine, 10 nM hydrocortisone, 5 $\mu$g/m insulin, 5 $\mu$g/ml human transferrin, 10 nM estradiol and 5 ng/ml selenium.

EXAMPLE 3

Induction of DDP Resistance

Resistance to DDP was induced by growing both the T-289 and the 2008 cells in culture in the continuous presence of DDP with or without TAM. Initial selections were performed at concentrations equivalent to the $IC^{90}$, i.e., the concentration producing inhibition of colony formation. Thus, the initial concentrations were 0.1, 0.25 and 0.5 $\mu$M DDP and 1.0, 2.5 and 5.0 $\mu$M TAM. The cells were allowed to grow to confluence (approximately 7 days) at which time successful cultures were split 1:4 and re-exposed to the same concentration of DDP±TAM. After 3 selections, the cells were exposed to incremental higher concentrations of DDP±TAM at the same ratio. Following each selection series, an aliquot of cells was removed, grown in drug-free media for 3 weeks and used in a colony forming assay to determine DDP sensitivity.

EXAMPLE 4

Colony Formation Assay

Cells were seeded into tissue culture dishes containing complete media (2008) or 0.2% agarose/media layered over a 1% agarose layer (T-289). Dishes received DDP at increasing concentrations and were incubated for 10 days at 37° with 5% $CO_2$. After 10 days, the colonies were counted, with each DDP concentration being expressed as a percentage of the drug-free control dishes.

Figure 3:
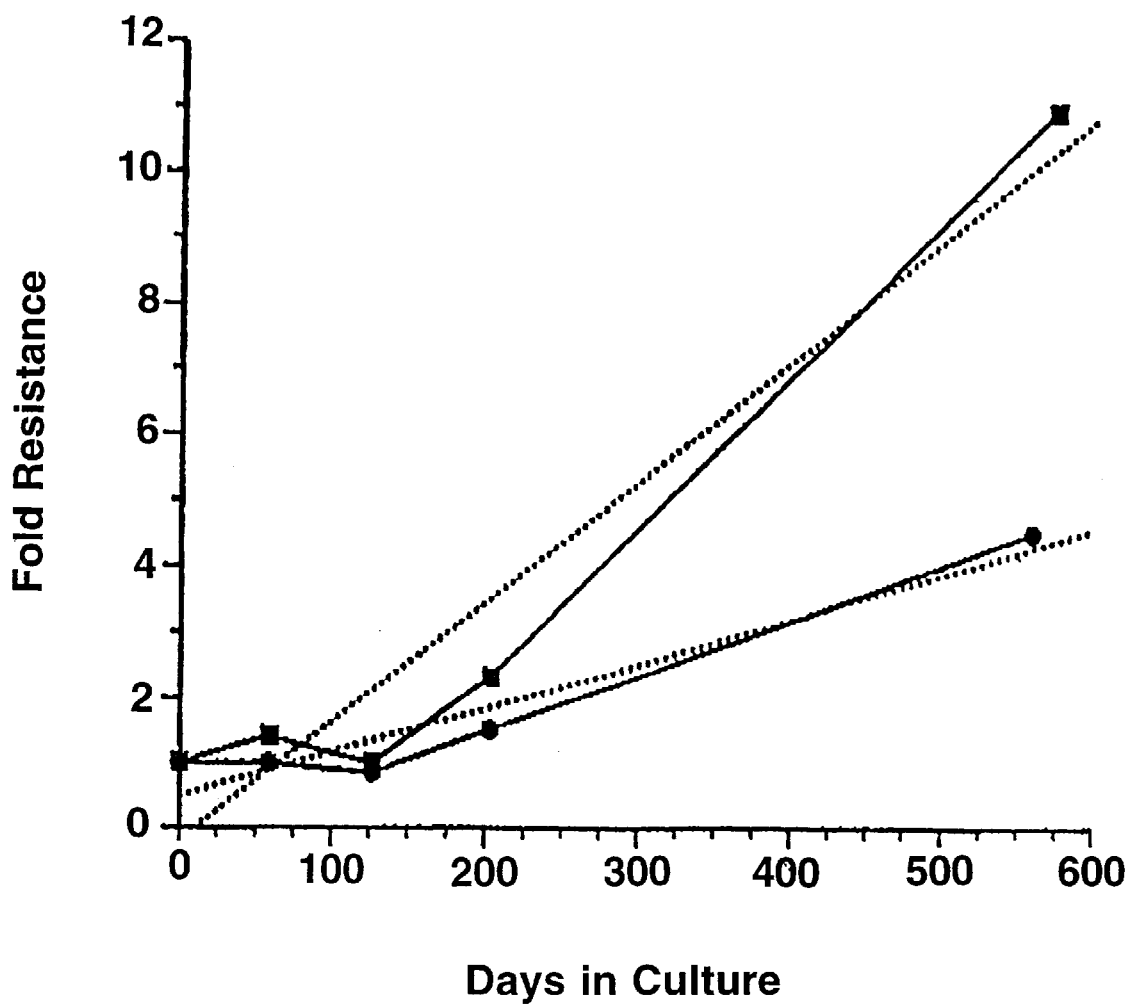
FIG. 3 shows the effect of TAM of the development of resistance to DDP in T-289 human melanoma cells (□, DDP alone; ●, DDP plus TAM). Each point represents DDP sensitivity relative to unselected T-289 cell determined from triplicate cultures.

FIG. 3 shows the time course for the development of resistance to DDP±TAM in the human melanoma T-289 cells. This cell line was relatively slow growing (doubling time 48–72 hours) and required a substantial amount of time to recover normal growth after each exposure to drug. DDP resistance became apparent after 200 days of selection, at which point, cells treated with DDP alone were 2.3-fold resistant to DDP. Cells treated with DDP plus TAM were only 1.5-fold resistant. Thereafter, DDP resistance emerged progressively at a rate that was 2.75 fold higher in the cells treated with DDP alone compared with those treated with DDP and TAM. The difference in the rate of development of resistance was statistically significant ($p<0.01$).

EXAMPLE 5

Effects of Tamoxifen on DDP-Resistant Cells

Figure 4:
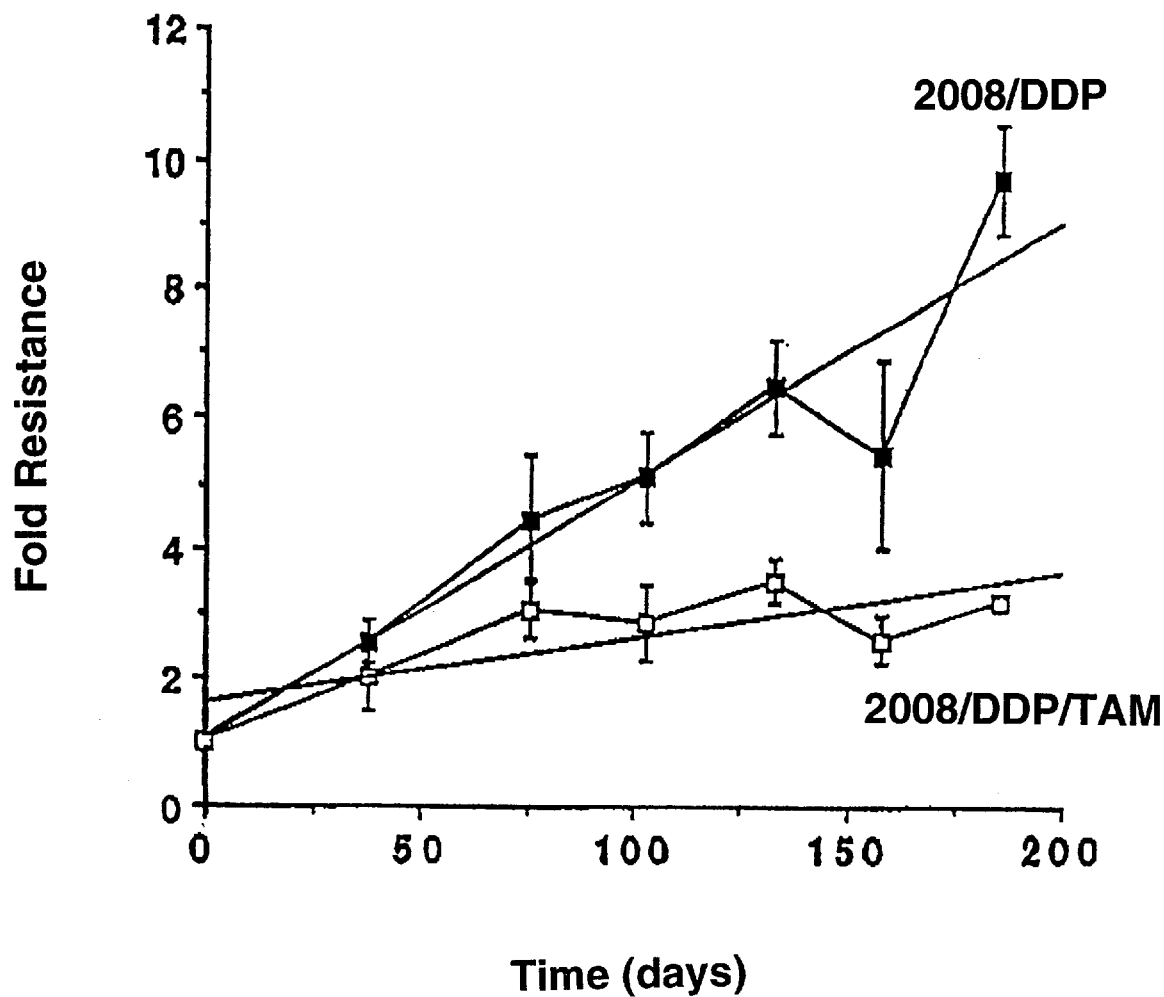
FIG. 4 shows the effect of TAM on the development of resistance to DDP in 2008 human ovarian carcinoma cells (■, DDP alone; □, DDP plus TAM). Each point represents the mean DDP sensitivity relative to unselected 2008 cells determine from 3 separate repeats of the experiment, each performed with triplicate cultures.

The 2008 cell line grew at a faster rate (doubling time 23 hours), which facilitated the repetition of the selection experiment. FIG. 4 shows that DDP resistance emerged as a linear function of time in this cell line. A difference in DDP sensitivity was apparent after selection in the lowest DDP concentration (38 days), and became statistically significant after 3 selections (103 days). The rate of development of resistance to DDP was reduced by TAM in each of the 3 repeats of this experiment. The mean ratio of the rate of development of resistance in the presence of DDP alone versus DDP plus TAM selections was 3.46±1.42 ($p<0.05$). Thus, in both the T-289 melanoma and 2008 ovarian carcinoma cell lines, concurrent exposure of cells to both DDP and TAM reduced the rate of development of resistance as well as the magnitude of the resistance.

The TAM-induced delay in the emergence of DDP resistance was not a result of those cultures receiving both agents having sustained greater cell kill, leaving fewer cells at risk for a somatic resistance-generating mutation. In example 3, cell cultures were allowed to recover normal growth rates and reach confluence before subsequent treatment. Thus, the same number of cells were exposed to selective pressure at each step. Therefore, greater cell kill per selection, by the drug combination was not responsible for TAM induced delay of DDP resistance development.

The present invention gives further insight into the complex nature of the interaction between TAM and DDP. TAM is synergistic with DDP not only in DDP sensitive tumors such as ovarian carcinoma and small cell lung cancer but also in melanoma, a tumor that is classically considered a DDP resistant tumor. Likewise, TAM can delay the development of DDP resistance in both a DDP-sensitive and DDP-resistant tumor type. Both the synergy and the delay in resistance development was observed at concentrations of TAM and DDP achievable in patients.

The present invention examined the nature of the interaction between the cytotoxic effects of DDP and TAM using the technique of median effect analysis. There is a highly synergistic interaction between these two drugs, not only with respect to the killing of a human melanoma cell line, but also in the case of human ovarian and small cell lung cancer cell lines in vitro.

EXAMPLE 6

Colony Forming Assay

The T-289 melanoma cell line and the 2008 cell line are the same as used in Example 3. The UMC 5 small cell lung cancer cell line is also of human origin. Cells were cultured as in Example 2.

Colony forming assays using a 1 hour drug exposure were performed by seeding cells onto 60 mm tissue culture dishes at 20,000 cells per dish and allowing 2 hours for them to attach. Drug was added to the dishes and incubated for 1 hour, then the dishes were washed and the cells were harvested by trypsinization, washed once to remove drug and resuspended in 5 ml of complete media containing 0.2% low melting-temperature agarose at 37° C. The cell suspension was mixed well, then aliquoted at 1 ml per dish in triplicate on to pre-prepared 35 mm dishes containing a basement layer of solidified 1% agarose. The cell containing layer was allowed to solidify at room temperature and the dishes were incubated at 37° C. in humidified 5% $CO_2$. Colonies greater than 124 $\mu$m were counted after 5 days. Colony forming assays using continuous exposure were performed by suspending cells in 0.2% agarose at 4000 cells/ml, aliquoting them into drug-containing tubes, then seeding these onto 35 mm dishes.

EXAMPLE 7

Median Effect Analysis

Median effect analysis was used to determine the nature of the interaction between TAM and DDP. The CI was determined from colony forming assays at increasing levels of cell kill. Drugs were combined at a ratio equal to the ratio of the $IC_{50}$, i.e., the CI at 50% cell kill, values for each drug determined by clonogenic assay. The combination was compared to the cytotoxicity of each drug alone in every experiment. Each data point represents the mean of a minimum of 3 experiments, each preformed with triplicate cultures.

EXAMPLE 8

Effects of TAM/DDP on Melanoma Cells

Figure 5:
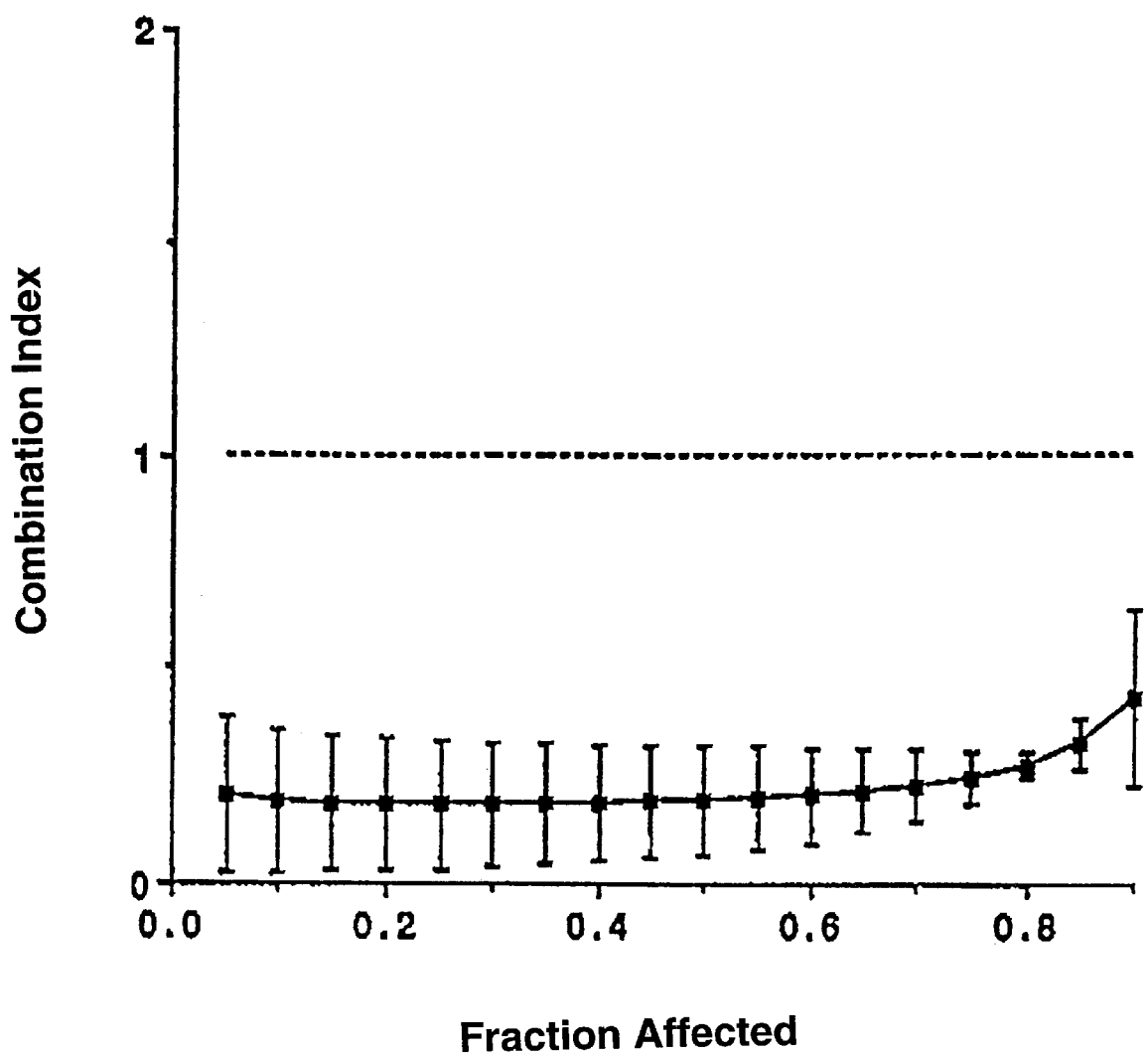
FIG. 5 shows the plot of the Combination Index (CI) as a function of cell kill for the interaction between DDP and TAM against human melanoma T-289 cells. Each data point represents the mean of a minimum of 3 experiments performed with triplicate cultures. Vertical bars are standard deviations (SD); where the bars are absent, the SD was less than the size of the symbol.

FIG. 5 shows the plot of the CI for the interaction between DDP and TAM for the T-289 melanoma cell line. The CI at 50% cell kill ($CI_{50}$) of 0.26±0.02 (SD) ($p<0.01$) demonstrates a marked synergism between TAM and DDP.

Effects of TAM/DDP on Ovarian Carcinoma Cells

Figure 6:
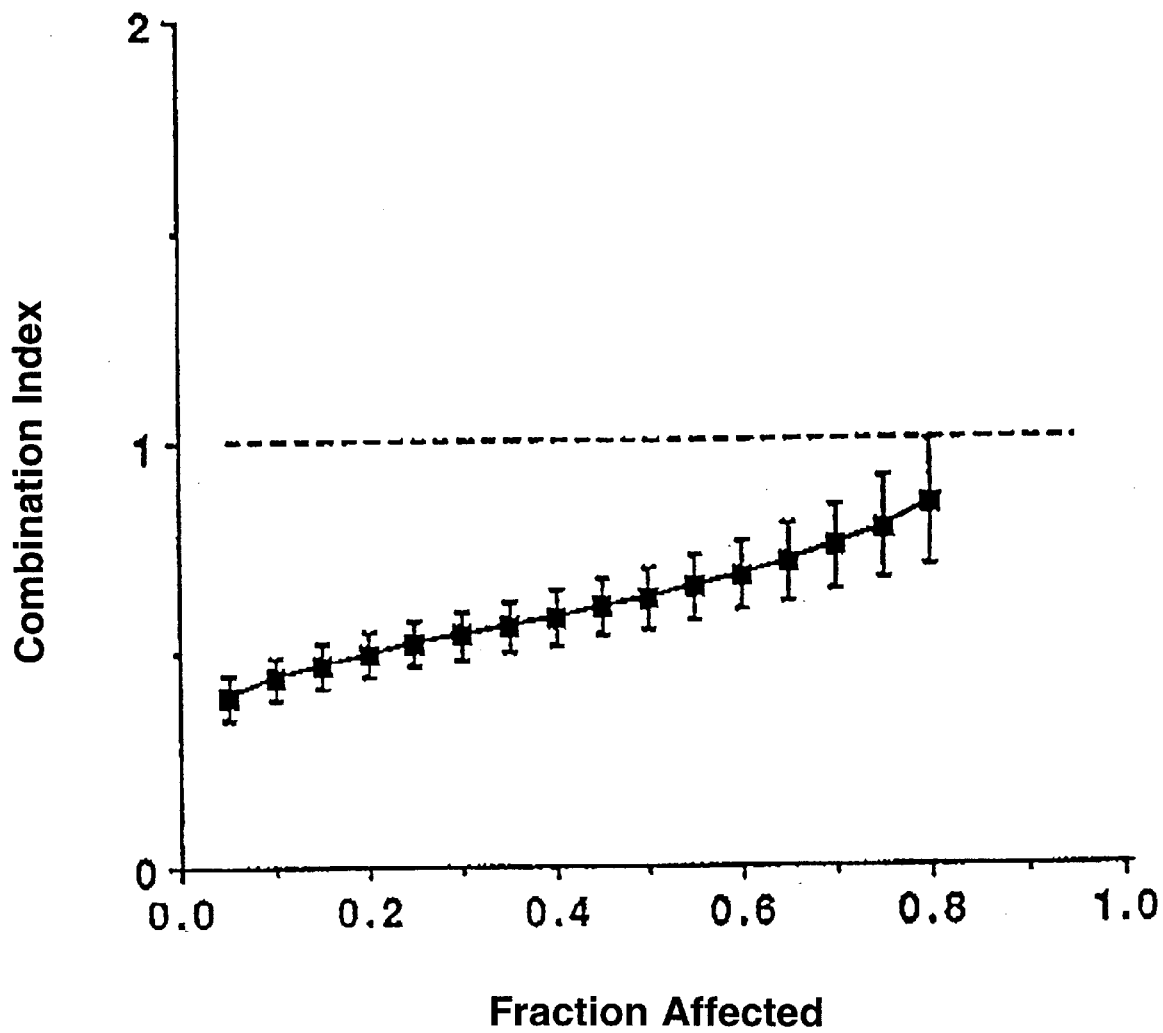
FIG. 6 shows the plot of the CI as a function of cell kill for the interaction between DDP and TAM against human ovarian 2008 cells. Each data point represents the mean of a minimum of 3 experiments performed with triplicate cultures. Vertical bars are SD.

FIG. 6 shows the CI plot for the combination of DDP and TAM for the human ovarian carcinoma cell line 2008. The combination was synergistic over the lower range of cell kill and yielded a $CI_{50}$ of 0.63±0.07 (SD) ($p<0.01$). Because of the counting error associated with high levels of cell kill (small numbers of surviving colonies) and because the interaction can only be analyzed over the portion of the dose-response where the curve for each agent alone and the combination curve is well fit. The CI plot is most reliable for the middle portion of the curve and relatively less reliable for cell kill >80%.

EXAMPLE 10
Effects of TAM/DDP on Small Coil Lung Cancer Cells

Figure 7:
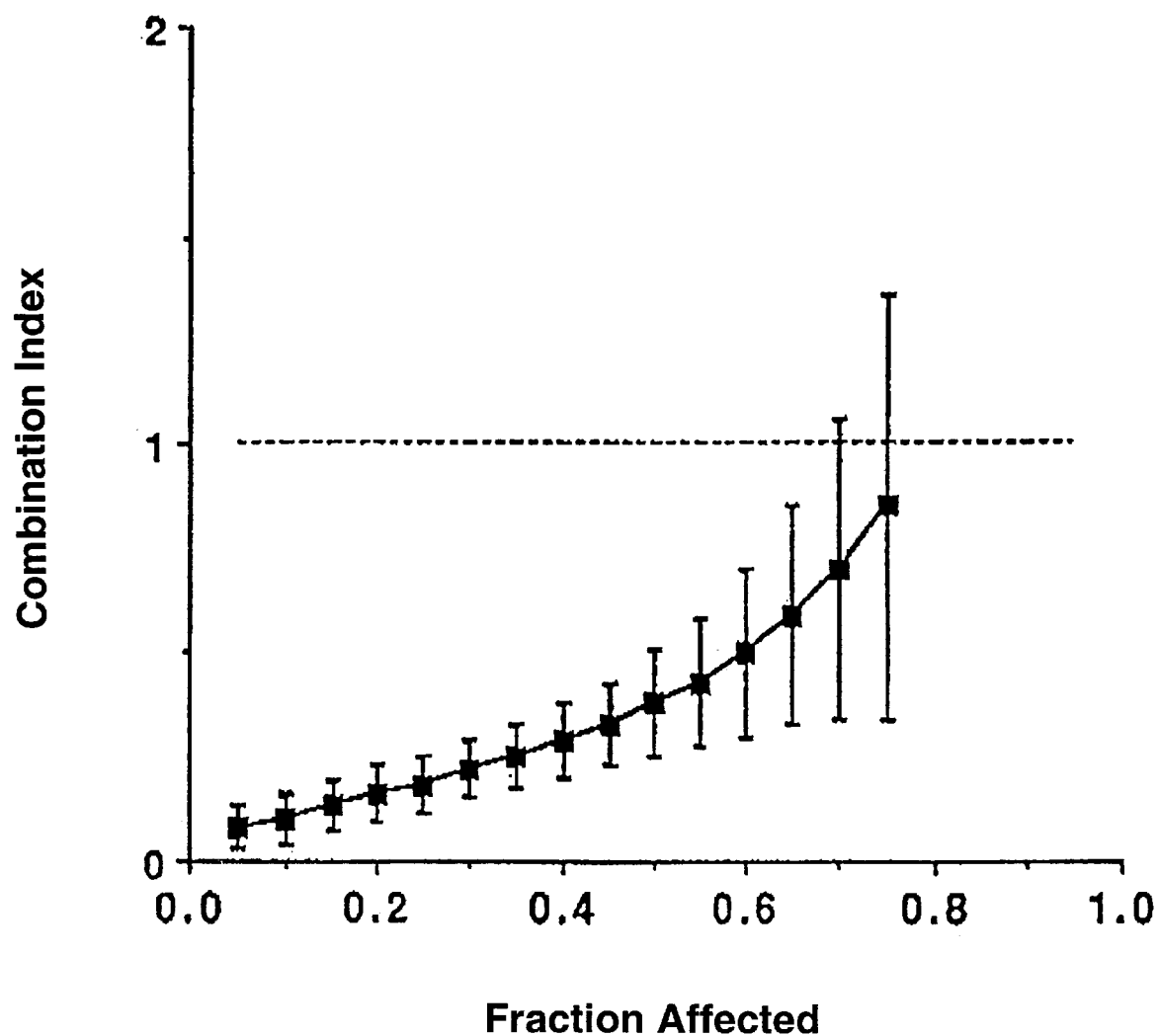
FIG. 7 shows the plot of the CI as a function of cell kill for the interaction between DDP and TAM against human small cell lung cancer UMC 5 cells. Each data point represents the mean of a minimum of 3 experiments performed with triplicate cultures. Vertical bars are SD.

The CI plot for the combination of DDP and TAM against the UMC small cell lung cancer line is shown in FIG. 7. The CI plot again illustrated a highly synergistic interaction and yielded a $CI_{50}$ value of $0.38 \pm 0.13$ (SD) ($p<0.01$).

The present invention demonstrates a highly synergistic interaction between TAM and DDP with respect to cytotoxicity towards human melanoma, ovarian carcinoma and small cell lung cancer cell lines.

Median effect analysis provides mathematically rigorous methodology for both identifying the nature of the interaction between two cytotoxic drugs and quantitating the magnitude of the interaction at different levels of cell kill. Median effect analysis identified the interaction as synergistic for these three human cell lines. The magnitude of the synergy was greater for both the melanoma line (CI50 0.26) and the small cell lung cancer line (CI50 0.38) than for the ovarian carcinoma line (0.63).

Several other features of the synergistic interaction are of potential clinical significance. For all three cell lines, synergy was clearly present even at the lowest levels of cell kill. Thus, TAM sensitizes tumor cells to DDP in vivo even under circumstances where DDP delivery to the tumor may be marginally adequate. Second, synergy was observed at concentrations of both DDP and TAM that are readily attainable in the plasma of patients treated with standard doses of these drugs.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of treating a cancer in vivo, wherein said cancer is selected from the group consisting of ovarian carcinoma, small lung cell carcinoma, testicular carcinoma, bladder cancer and squamous cell cancer of the head and neck, comprising administering to an individual having said cancer, a pharmacological dose of a combination of a carboplatin and tamoxifen, wherein said carboplatin and tamoxifen exert a synergistic anti-tumor effect on said cancer.

2. A method of killing nonmelanoma neoplastic cells in bone marrow, wherein said cells are derived from a cancer selected from the group consisting of ovarian carcinoma, small lung cell carcinoma, testicular carcinoma, bladder cancer and squamous cell cancer of the head and neck, comprising the steps of removing bone marrow from an individual having said cancer; contacting said bone marrow with a cytocidally synergistic effective dose of carboplatin and tamoxifen, wherein said tamoxifen is administered in an amount from 0.1 $\mu$M to 1 $\mu$M; and returning said contacted bone marrow to said individual.

* * * * *

UNITED STATES PATENT AND TRADEMARK OFFICE
CERTIFICATE OF CORRECTION

PATENT NO. : 6,288,111 B1
DATED : September 11, 2001
INVENTOR(S) : Edward F. McClay and Stephen B. Howell It is certified that error appears in the above-identified patent and that said Letters Patent is hereby corrected as shown below:

Column 2,
Lines 21 and 26, please insert -- a -- between the words "provided" and "method".

Column 3,
Line 1, "determine" should read -- determined --.
Line 35, "that" should read -- than --.

Column 4,
Line 2, "is" should read -- are --.

Column 7,
Line 4, "received" should read -- receive --.

Column 10,
Line 55, please insert the line -- EXAMPLE 9 -- before the line reading "Effects of TAM/DDP on Ovarian Carcinoma Cells".
Line 62, please insert the word -- of -- between the words "because" and "the".

Column 11,
Line 1, "coil" should read -- cell --.

Signed and Sealed this

First Day of October, 2002

Attest:

*Attesting Officer*

JAMES E. ROGAN
*Director of the United States Patent and Trademark Office*